US011317895B2

(12) United States Patent
Jeon et al.

(10) Patent No.: US 11,317,895 B2
(45) Date of Patent: May 3, 2022

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Hyunjae Jeon, Seongnam-si (KR); Dongkuk Shin, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 228 days.

(21) Appl. No.: 16/507,628

(22) Filed: Jul. 10, 2019

(65) Prior Publication Data

US 2020/0205785 A1 Jul. 2, 2020

(30) Foreign Application Priority Data

Dec. 27, 2018 (KR) .......................... 10-2018-0170877

(51) Int. Cl.
*A61B 8/08* (2006.01)
*A61B 8/00* (2006.01)
(Continued)

(52) U.S. Cl.
CPC .......... *A61B 8/5207* (2013.01); *A61B 8/4444* (2013.01); *A61B 8/463* (2013.01);
(Continued)

(58) Field of Classification Search
CPC ....... G06T 7/11; G06T 7/12; A61B 2090/378; A61B 8/5207; A61B 8/4444; A61B 8/463;
(Continued)

(56) References Cited

U.S. PATENT DOCUMENTS 4,877,033 A  10/1989  Seitz, Jr.
8,237,784 B2  8/2012  Kim et al.
(Continued)

FOREIGN PATENT DOCUMENTS

EP       3363368 A1    8/2018
JP    2011-104079 A    6/2011
(Continued)

OTHER PUBLICATIONS

T. D. Deutch and A. Z. Abuhamad, Sonography-Based Automated Volume Count (SonoAVC): an Efficient and Reproducible Method of Follicular Assessment, General Electric Company, 2007, [online] Available: http://www.predictweb.it/wp-content/uploads/SonoAVC.pdf. (Year: 2007).*

(Continued)

*Primary Examiner* — Joseph M Santos Rodriguez
*Assistant Examiner* — Kaitlyn E Selmer
(74) *Attorney, Agent, or Firm* — Sughrue Mion, PLLC

(57) ABSTRACT

A method of operating an ultrasound diagnosis apparatus includes: obtaining a three-dimensional (3D) ultrasound image including an ovarian region; detecting, based on at least one parameter used for extracting a particular oocyte, a plurality of candidate ovarian follicles from which mature oocytes are more likely to be extracted in the 3D ultrasound image; registering a two-dimensional (2D) ultrasound image corresponding to a first cross-section of the ovarian region to the 3D ultrasound image; and guiding, based on a result of the registering, a position of at least one candidate ovarian follicle from which an oocyte is to be extracted in the 2D ultrasound image.

16 Claims, 13 Drawing Sheets

(51) Int. Cl.
  *A61B 90/00*  (2016.01)
  *A61B 8/12*  (2006.01)
  *A61B 8/14*  (2006.01)
(52) U.S. Cl.
  CPC . *A61B 8/12* (2013.01); *A61B 8/14* (2013.01); *A61B 8/5223* (2013.01); *A61B 2090/378* (2016.02)
(58) Field of Classification Search
  CPC .......... A61B 8/12; A61B 8/14; A61B 8/5223; A61B 8/483; A61B 8/085
  See application file for complete search history.

(56) References Cited

U.S. PATENT DOCUMENTS

2011/0152684 A1* 6/2011 Altmann .................. A61B 8/12
                                                                              600/443
2016/0063695 A1* 3/2016 Lee ........................ A61B 8/463
                                                                              382/131
2017/0061607 A1* 3/2017 Eskandari ................. G06T 5/30
2018/0110554 A1* 4/2018 Zarins ................ A61B 18/1485
2019/0307417 A1* 10/2019 Subbarao ............. G06K 9/6224

FOREIGN PATENT DOCUMENTS

| JP | 2011-224143 A | 11/2011 |
| KR | 10-1014562 B1 | 2/2011 |
| WO | 2015119338 A1 | 8/2015 |

OTHER PUBLICATIONS

Communication dated Jan. 13, 2020, from the European Patent Office in counterpart European Application No. 19181541.4.

* cited by examiner

ULTRASOUND DIAGNOSIS APPARATUS AND METHOD OF OPERATING THE SAME

CROSS-REFERENCE TO RELATED APPLICATION(S)

This application is based on and claims priority under 35 U.S.C. § 119 to Korean Patent Application No. 10-2018-0170877, filed on Dec. 27, 2018, in the Korean Intellectual Property Office, the disclosure of which is incorporated by reference herein in its entirety.

BACKGROUND

1. Field

The disclosure relates to ultrasound diagnosis apparatuses and methods of operating the same.

2. Description of Related Art

Ultrasound diagnosis apparatuses transmit, to an object, ultrasound signals generated by transducers of a probe and detect information about signals reflected from the object, thereby obtaining at least one image of an internal part, for example, soft tissue or blood flow, of the object.

SUMMARY

Provided are ultrasound diagnosis apparatuses and methods whereby when an oocyte is extracted from an ovarian follicle, follicles where oocytes have been extracted may be easily distinguished from follicles where oocytes have not been extracted, thereby allowing a user to accurately and promptly perform an oocyte extraction procedure.

Additional aspects will be set forth in part in the description which follows and, in part, will be apparent from the description, or may be learned by practice of the presented embodiments.

In accordance with an aspect of the disclosure, a method of operating an ultrasound diagnosis apparatus includes: obtaining a three-dimensional (3D) ultrasound image including an ovarian region; detecting, based on at least one parameter used for extracting a particular oocyte, a plurality of candidate ovarian follicles from which mature oocytes are more likely to be extracted in the 3D ultrasound image; registering a two-dimensional (2D) ultrasound image corresponding to a first cross-section of the ovarian region to the 3D ultrasound image; and guiding, based on a result of the registering, a position of at least one candidate ovarian follicle from which an oocyte is to be extracted in the 2D ultrasound image.

In accordance with another aspect of the disclosure, an ultrasound diagnosis apparatus includes: a probe configured to transmit ultrasound signals to an ovarian region of an object and receive echo signals reflected from the ovarian region; a processor configured to obtain a 3D ultrasound image including the ovarian region based on the echo signals, detect, based on at least one parameter used for extracting a particular oocyte, a plurality of candidate ovarian follicles from which mature oocytes are more likely to be extracted in the 3D ultrasound image, register a 2D ultrasound image corresponding to a first cross-section of the ovarian region to the 3D ultrasound image, and guide, based on a result of the registering, a position of at least one candidate ovarian follicle from which an oocyte is to be extracted in the 2D ultrasound image; a display displaying information for guiding the position of the at least one candidate ovarian follicle; and an oocyte extractor configured to extract an oocyte from the at least one candidate ovarian follicle.

In accordance with another aspect of the disclosure, provided is a computer program stored in a computer-readable recording medium to perform a method in combination with an ultrasound diagnosis apparatus, the method including: obtaining a 3D ultrasound image including an ovarian region; detecting, based on at least one parameter used for extracting a particular oocyte, a plurality of candidate ovarian follicles from which mature oocytes are more likely to be extracted in the 3D ultrasound image; registering a 2D ultrasound image corresponding to a first cross-section of the ovarian region to the 3D ultrasound image; and guiding, based on a result of the registering, a position of at least one candidate ovarian follicle from which an oocyte is to be extracted in the 2D ultrasound image.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
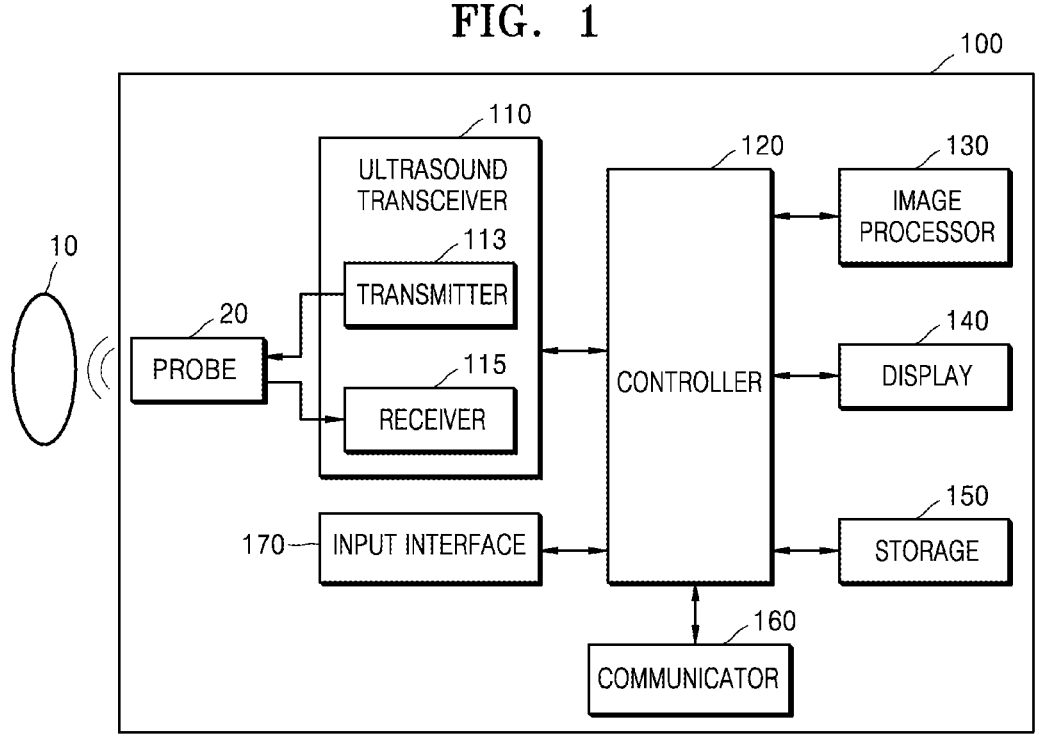
FIG. 1 is a block diagram of a configuration of an ultrasound diagnosis apparatus according to an embodiment.

Certain exemplary embodiments are described in greater detail below with reference to the accompanying drawings.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail. Like reference numerals refer to like elements throughout. The present specification does not describe all components in the embodiments, and common knowledge in the art or the same descriptions of the embodiments will be omitted below. Terms such as "part" and "portion" used herein denote those that may be embodied by software or hardware. According to exemplary embodiments, a plurality of parts or portions may be embodied by a single unit or element, or a single part or portion may include a plurality of elements. Expressions such as "at least one of," when preceding a list of elements, modify the entire list of elements and do not modify the individual elements of the list. Hereinafter, the principles and embodiments of the present disclosure will be described in detail with reference to the accompanying drawings.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus that is portable, moveable, mobile, or hand-held. Examples of the portable-type ultrasound diagnosis apparatus may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control an ultrasound receiver 115 to generate ultrasound data by converting reception signals received from the probe 20 from analog to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

Figure 2C:
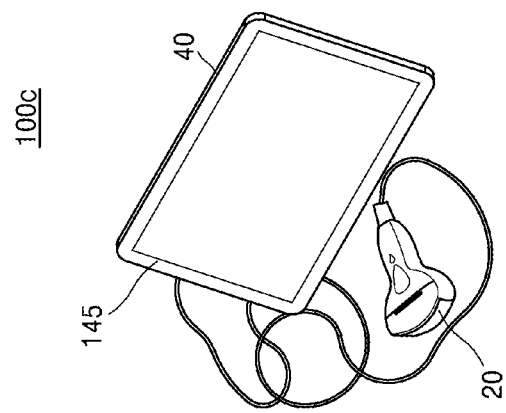
FIGS. 2A through 2C illustrate ultrasound diagnosis apparatuses according to embodiments.
Figure 2B:
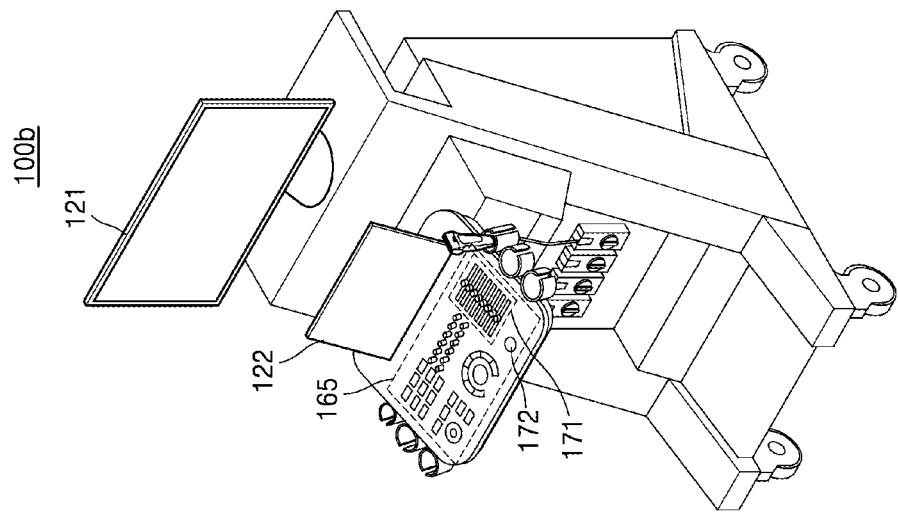
Figure 2A:
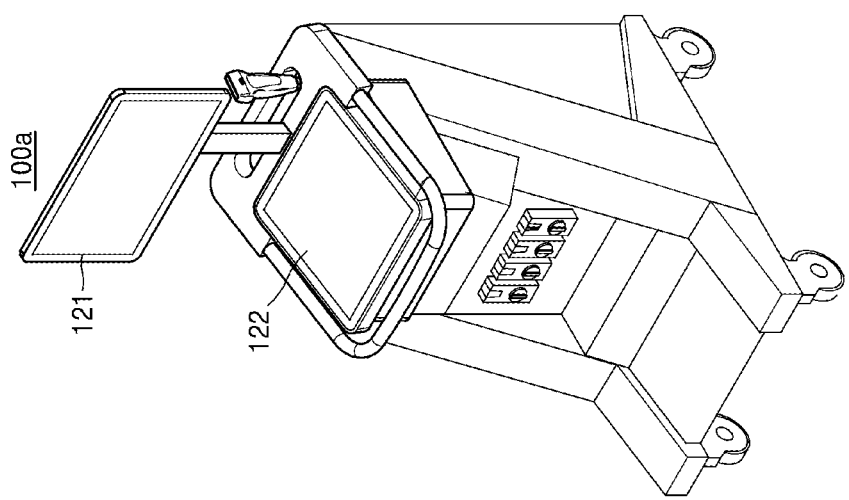

FIGS. 2A, 2B, and 2C are diagrams illustrating an ultrasound diagnosis apparatus according to an exemplary embodiment.

Referring to FIGS. 2A and 2B, the ultrasound diagnosis apparatus 100a or 100b may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100a or 100b. The main display 121 and the sub-display 122 may provide graphical user interfaces (GUI), thereby receiving user's inputs of data to control the ultrasound diagnosis apparatus 100a or 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100a or 100b may control the display of the ultrasound image on the main display 121 by using the input control data.

Referring to FIG. 2B, the ultrasound diagnosis apparatus 100b may include a control panel 165. The control panel 165 may include buttons, trackballs, jog switches, or knobs, and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100b may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100c may include a portable device. An example of the portable ultrasound diagnosis apparatus 100c may include smart phones including probes and applications, laptop computers, personal digital assistants (PDAs), or tablet PCs, but an exemplary embodiment is not limited thereto.

The ultrasound diagnosis apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100c, and a GUI.

Figure 3:
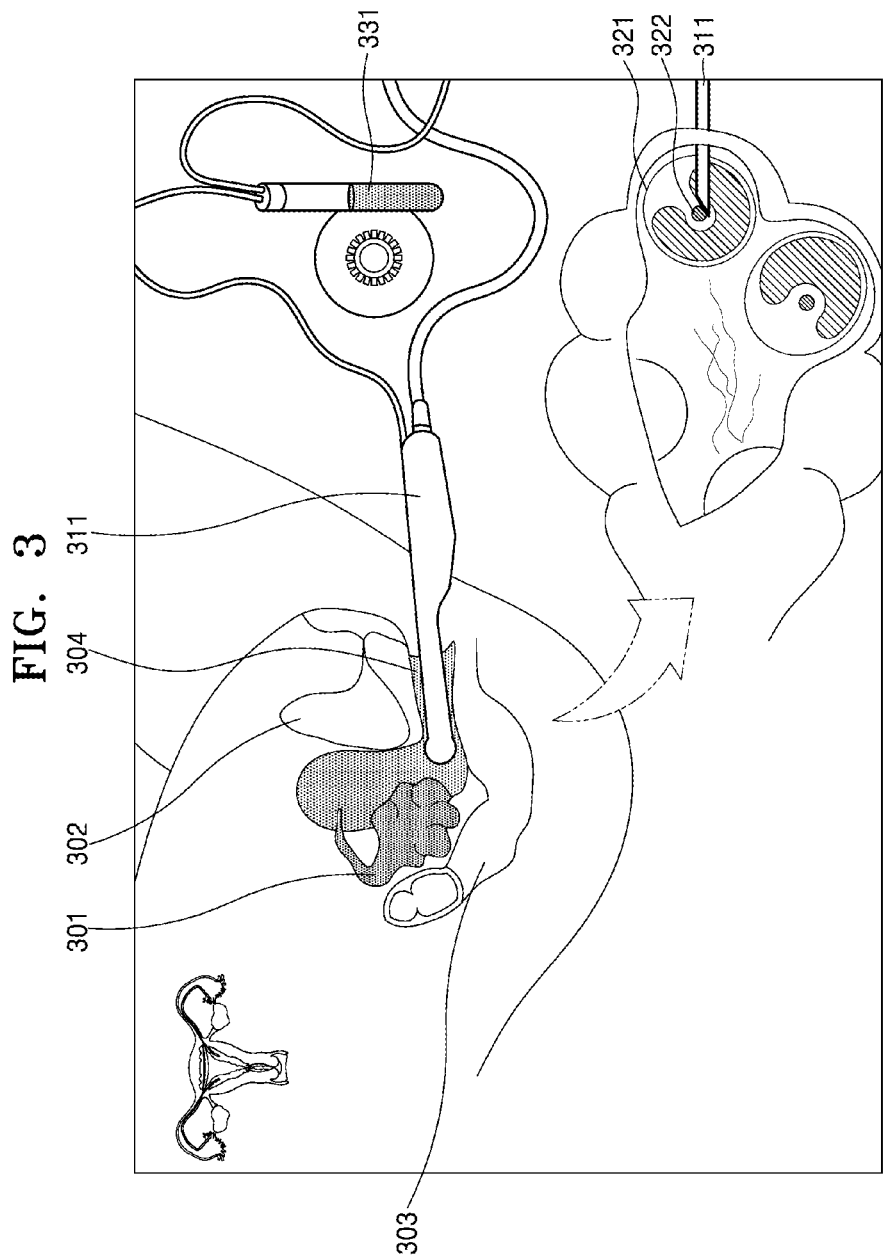
FIG. 3 illustrates a process of extracting an oocyte from a follicle by using an ultrasound diagnosis apparatus, according to an embodiment.

FIG. 3 illustrates a process of extracting an oocyte from an ovarian follicle (hereinafter, referred to as a 'follicle') by using the ultrasound diagnosis apparatus (100 of FIG. 1), according to an embodiment.

FIG. 3 shows a human body structure including an ovarian region. Structures such as a bladder 302 and a large intestine 303 are in close proximity to an ovary 301. Mature oocytes are needed for artificial insemination, and superovulation may be induced by a medicine to increase the success rates of artificial insemination. When superovulation is induced, a plurality of follicles may remain in the ovary 301. The user may insert an oocyte extractor 311 into a vagina 304 and extract an oocyte 322 from a follicle 321 within the ovary 301 via the oocyte extractor 311. The extracted oocyte 322 may then be stored in a repository such as a test tube 331.

The ultrasound diagnosis apparatus 100 may obtain an ultrasound image based on ultrasound data including an ovarian region. The ultrasound diagnosis apparatus 100 may display the obtained ultrasound image. The user may extract an oocyte from a follicle while examining the ultrasound image displayed by the ultrasound diagnosis apparatus 100. In this case, because a follicle from which an oocyte has been extracted is not easily distinguished from a follicle where an oocyte has not been extracted, the user may mistakenly attempt to extract an oocyte from a follicle where an oocyte has already been extracted.

Thus, by displaying tracking information indicating tracking of follicles from which oocytes have been extracted and from which oocytes have not been extracted, the ultrasound diagnosis apparatus 100 may guide the user to perform an oocyte extraction procedure more accurately and quickly.

Figure 4:
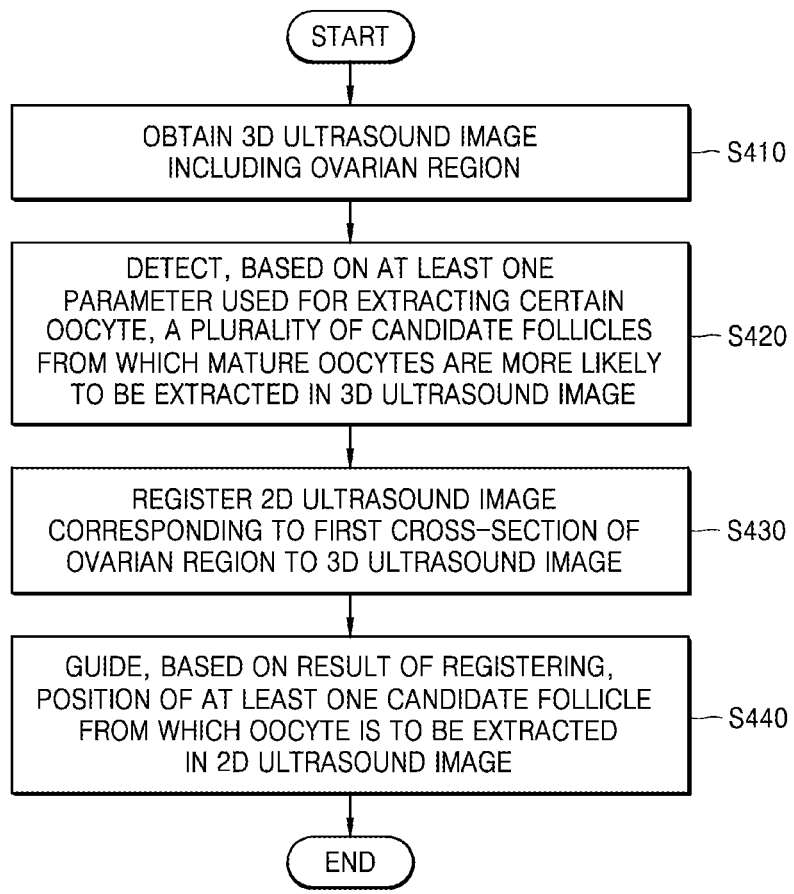
FIG. 4 is a flowchart of a method of operating an ultrasound diagnosis apparatus, according to an embodiment.

FIG. 4 is a flowchart of a method of operating the ultrasound diagnosis apparatus 100, according to an embodiment.

Referring to FIG. 4, the ultrasound diagnosis apparatus 100 may obtain a three-dimensional (3D) ultrasound image including an ovarian region (S410).

The ultrasound diagnosis apparatus 100 may detect, based on at least one parameter used for extracting a certain oocyte, a plurality of candidate follicles from which mature oocytes are more likely to be extracted in the 3D ultrasound image (S420).

For example, the ultrasound diagnosis apparatus 100 may acquire a value of at least one parameter from the 3D ultrasound image. In this case, the at least one parameter may be a parameter used for measuring at least one of a size of an ovary and a length and a volume of a follicle, but is not limited thereto. The ultrasound diagnosis apparatus 100 may detect a follicle for which a value of at least one parameter satisfies a preset range as a candidate follicle.

The ultrasound diagnosis apparatus 100 may register a two-dimensional (2D) ultrasound image corresponding to a first cross-section of the ovarian region to the 3D ultrasound image (S430).

For example, the ultrasound diagnosis apparatus 100 may register a 2D ultrasound image to the 3D ultrasound image, based on a value of at least one parameter for a plurality of candidate follicles detected in the 3D ultrasound image.

A size of a follicle may be observed to be less than its original size according to a position of a cross-section corresponding to a 2D ultrasound image. Thus, when an oocyte is extracted from a follicle by using only a 2D ultrasound image, a size of the follicle may be mistakenly determined and confusion may occur when tracking the same follicle. The ultrasound diagnosis apparatus 100 may register the 2D ultrasound image to the 3D ultrasound image based on information about candidate follicles detected in the 3D ultrasound image, thereby allowing accurate and prompt tracking of positions of the candidate follicles.

In addition, registration between the 2D and 3D ultrasound images may be performed based on a value of a parameter in the 3D ultrasound image and a sensor.

The ultrasound diagnosis apparatus 100 may guide, based on a result of the registering, a position of at least one candidate follicle from which an oocyte is to be extracted in the 2D ultrasound image (S440).

For example, the ultrasound diagnosis apparatus 100 may identify, based on a result of the registering, a position of at least one candidate follicle from which an oocyte is to be extracted in the 2D ultrasound image, and display the position of the at least one candidate follicle. When a first oocyte is extracted from a first candidate follicle among the at least one candidate follicle, the ultrasound diagnosis apparatus 100 may display, on the 2D ultrasound image, information indicating that the first oocyte has been extracted from the first candidate follicle.

For example, the ultrasound diagnosis apparatus 100 may display a contour line or color of the first candidate follicle differently from a contour line or color of another candidate follicle from which an oocyte has not been extracted, such that the first candidate follicle is distinguished from the other candidate follicle.

For example, as an oocyte is extracted from at least one candidate follicle in the 2D ultrasound image, the ultrasound diagnosis apparatus 100 may display on the 2D ultrasound image, tracking information indicating tracking of candidate follicles from which oocytes have been extracted and candidate follicles from which oocytes have not been extracted.

For example, the ultrasound diagnosis apparatus 100 may acquire position information of at least one structure based on an anatomical structure within the ovarian region. In this case, the at least one structure may be a cyst, an intima, a vessel, etc., but is not limited thereto. The ultrasound diagnosis apparatus 100 may identify an anatomical structure within the ovarian region based on the 3D ultrasound image and acquire position information of at least one structure based on the anatomical structure. The ultrasound diagnosis apparatus 100 may guide, based on the position information of the at least one structure, a route along which an oocyte is to be extracted from at least one candidate follicle.

For example, after the first oocyte is extracted from the first candidate follicle from among the at least one candidate follicle, the ultrasound diagnosis apparatus 100 may guide a position of a second candidate follicle from which a second oocyte is subsequently to be extracted in the 2D ultrasound image.

In addition, as an oocyte is extracted from at least one candidate follicle in the 2D ultrasound image, the ultrasound diagnosis apparatus 100 may display a plurality of candidate follicles on the 3D ultrasound image in such a manner that candidate follicles where oocytes have been extracted are distinguished from candidate follicles where oocytes have not been extracted.

Furthermore, the ultrasound diagnosis apparatus 100 may display, on the 3D ultrasound image, a position of the first cross-section corresponding to the 2D ultrasound image.

Furthermore, the ultrasound diagnosis apparatus 100 may determine, based on positions of a plurality of candidate follicles, a priority order of cross-sections according to a decreasing order of probability of detecting a candidate follicle from an ovarian region. The ultrasound diagnosis apparatus 100 may obtain 2D ultrasound images according to the priority order of cross-sections.

When an oocyte extraction procedure is performed, the ultrasound diagnosis apparatus 100 may track positions of candidate follicles in the 2D ultrasound image, based on information about candidate follicles acquired from the 3D ultrasound image When an oocyte is extracted from a certain follicle, the ultrasound diagnosis apparatus 100 may display the candidate follicle where the oocyte has been extracted to be distinguished from a candidate follicle where an oocyte has not been extracted, thereby allowing the user to perform a prompt and accurate extraction procedure.

Figure 5:
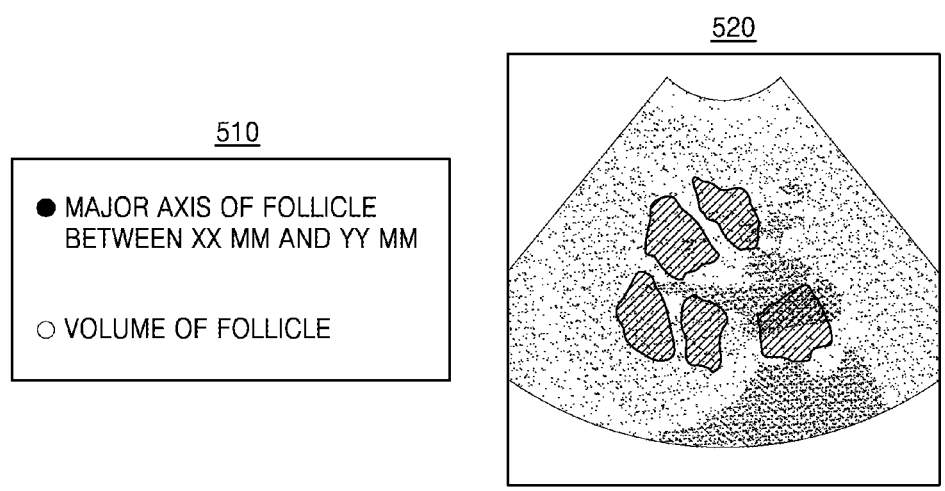
FIG. 5 illustrates a process by which an ultrasound diagnosis apparatus detects candidate ovarian follicles from which mature oocytes are more likely to be extracted, according to an embodiment.

FIG. 5 illustrates a process by which the ultrasound diagnosis apparatus 100 detects candidate follicles from which mature oocytes are more likely to be extracted, according to an embodiment.

Referring to an image 510 of FIG. 5, the ultrasound diagnosis apparatus 100 may display a screen for setting a parameter used for detecting candidate follicles from which mature oocytes are more likely to be extracted.

In this case, a parameter may be used to measure at least one of a size of an ovary and a size and a volume of a follicle. For example, a parameter used to measure the size of a follicle may be a major axis length of the follicle.

The ultrasound diagnosis apparatus 100 may receive an input of selecting a parameter used to detect a candidate follicle as well as an input of setting a range of values for the selected parameter. For example, as shown in the image 510 of FIG. 5, the ultrasound diagnosis apparatus 100 may receive an input of selecting a major axis length of a follicle from among a plurality of parameters. When a major axis length of a follicle is selected, an input field for setting the major axis length of the follicle may be displayed. For example, the ultrasound diagnosis apparatus 100 may receive an input of setting a major axis length of a follicle to a range between XX millimeters (mm) and YY mm. As another example, the ultrasound diagnosis apparatus 100 may receive an input of setting the major axis length of the follicle to be XX mm or more.

As another example, the ultrasound diagnosis apparatus 100 may receive an input of selecting a major axis length and a volume of a follicle as parameters. The ultrasound diagnosis apparatus 100 may receive an input of setting ranges of a major axis length and a volume with respect to a follicle for detection of a candidate follicle.

The ultrasound diagnosis apparatus 100 may acquire a value of at least one parameter from a 3D ultrasound image including an ovarian region. The ultrasound diagnosis apparatus 100 may detect a follicle for which a value of at least one parameter satisfies a preset range as a candidate follicle.

For example, when a parameter is a major axis length of a follicle and a range of values for the parameter is set to be 16 mm or more, the ultrasound diagnosis apparatus 100 may detect a follicle having a major axis length of 16 mm or more as a candidate follicle. The ultrasound diagnosis apparatus 100 may display only candidate follicles detected in the 3D ultrasound image.

In addition, as shown in an image 520 of FIG. 5, the ultrasound diagnosis apparatus 100 may acquire a 2D ultrasound image corresponding to a first cross-section of the ovarian region. In this case, the ultrasound diagnosis apparatus 100 may register the 2D ultrasound image to the 3D ultrasound image based on a value of a parameter for candidate follicles detected in the 3D ultrasound image. For example, the ultrasound diagnosis apparatus 100 may display, based on the 3D ultrasound image, candidate follicles having a major axis length of 16 mm or more on the 2D ultrasound image.

Figure 6:
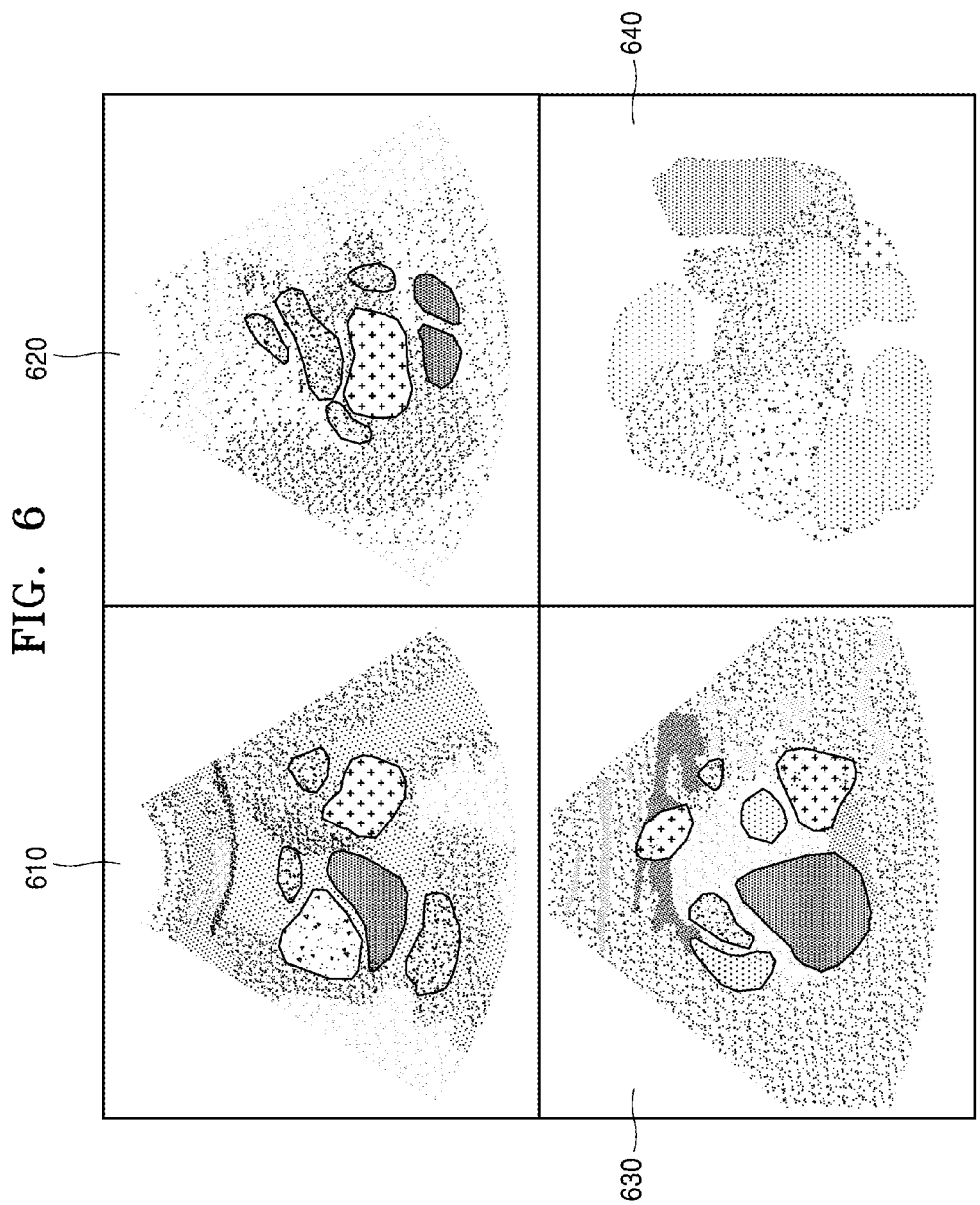
FIG. 6 illustrates a three-dimensional (3D) ultrasound image including an ovarian region and two-dimensional (2D) ultrasound images according to an embodiment.

FIG. 6 illustrates a 3D ultrasound image 640 including an ovarian region and 2D ultrasound images 610, 620, and 630 respectively corresponding to cross-sections of the ovarian region, according to an embodiment.

The ultrasound diagnosis apparatus 100 may receive echo signals reflected from an ovarian region via a probe. The ultrasound diagnosis apparatus 100 may perform analog-to-digital (ADC) conversion on the echo signals to generate digital signals. The ultrasound diagnosis apparatus 100 may perform reception focusing on the digital signals to generate a focused reception signal and acquire ultrasound data corresponding to a frame by using the focused reception signal. In this case, a frame may be a 2D ultrasound image corresponding to a predetermined cross-section of an ovarian region. The ultrasound diagnosis apparatus 100 may generate volume data based on the ultrasound data. The volume data may be composed of frames and include voxels having brightness values. The ultrasound diagnosis apparatus 100 may obtain a 3D ultrasound image by rendering the volume data.

Referring to FIG. 6, the ultrasound diagnosis apparatus 100 may display candidate follicles on the 3D ultrasound image 640.

The ultrasound diagnosis apparatus 100 may display the 2D ultrasound images 610, 620, and 630 respectively corresponding to predetermined cross-sections in the 3D ultrasound image 640. The 2D ultrasound images 610, 620, and 630 may respectively correspond to first through third cross-sections of the ovarian region.

For example, the first through third cross-sections may be adjacent cross-sections of the ovarian region. Furthermore, the first through third cross-sections may be cross-sections of the ovarian region where candidate follicles are more likely to be detected. In addition, the first through third cross-sections may be cross-sections of the ovarian region that are preset by the user based on an anatomical structure of the ovarian region.

The ultrasound diagnosis apparatus 100 may display on each of the 2D ultrasound images 610, 620, and 630 candidate follicles detected as follicles from which mature oocytes are more likely to be extracted. For example, the ultrasound diagnosis apparatus 100 may display a contour line of each candidate follicle as a bold line. Contour lines of candidate follicles from which oocytes are to be extracted may be displayed as bold lines to allow the user to easily identify positions of the candidate follicles.

As shown in FIG. 6, the ultrasound diagnosis apparatus 100 may display the 3D ultrasound image 640 including the ovarian region, together with the 2D ultrasound images 610, 620, and 630 respectively corresponding to the predetermined cross-sections of the ovarian region. Furthermore, the ultrasound diagnosis apparatus 100 may respectively display position information of the candidate follicles on the 2D and 3D ultrasound images 610, 620, 630, and 640. For example, the ultrasound diagnosis apparatus 100 may display position information of the candidate follicles on the 2D and 3D ultrasound images 610, 620, 630, and 640 by displaying the candidate follicles in colors, marking contour lines of the candidate follicles, or assigning reference numbers to the candidate follicles.

Figure 7:
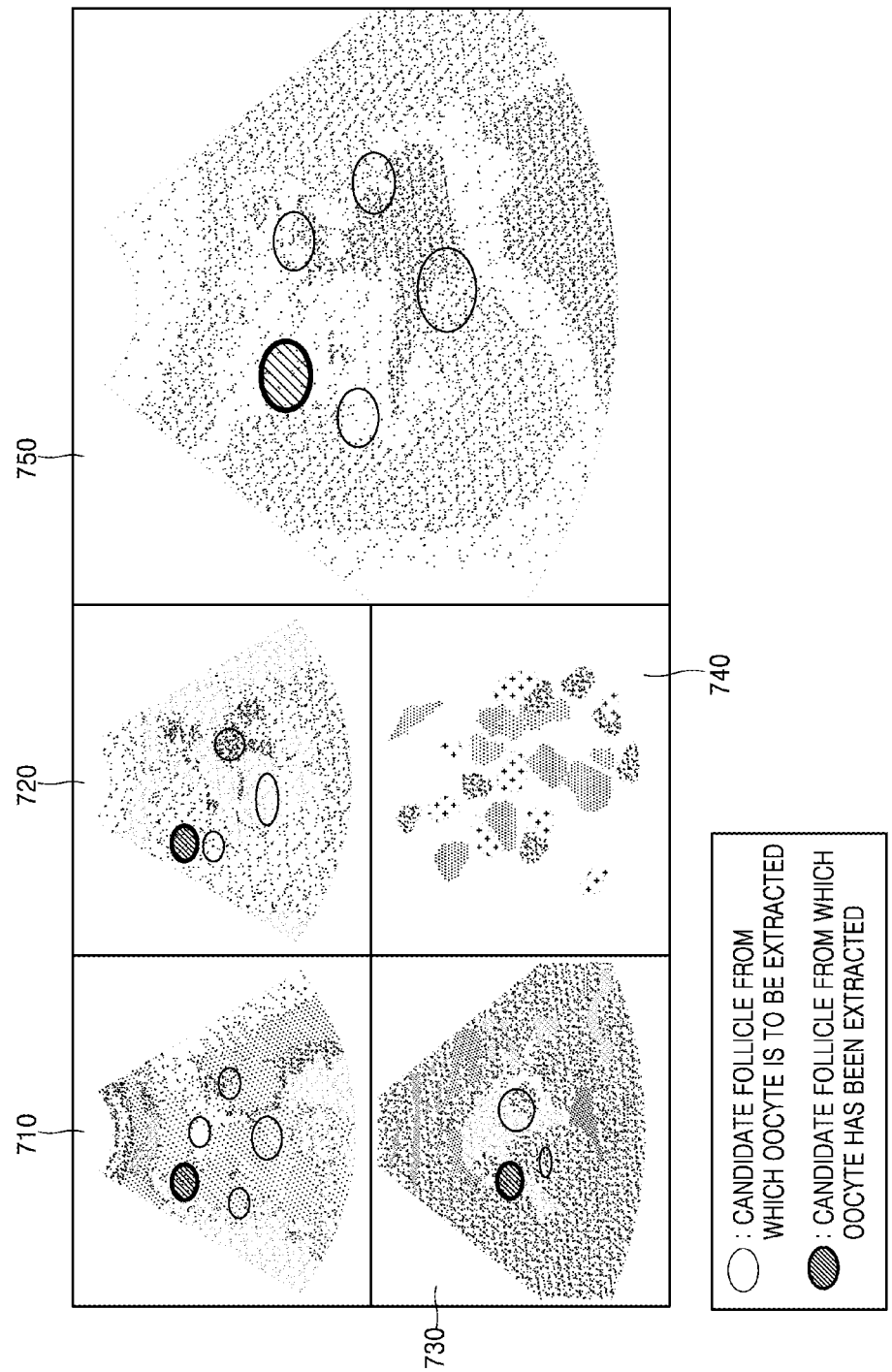
FIG. 7 illustrates a process by which an ultrasound diagnosis apparatus guides a position of a candidate ovarian follicle, according to an embodiment.

FIG. 7 illustrates a process by which the ultrasound diagnosis apparatus 100 guides a position of a candidate follicle, according to an embodiment.

The ultrasound diagnosis apparatus 100 may register a 2D ultrasound image corresponding to a first cross-section of an ovarian region to a 3D ultrasound image. In detail, the ultrasound diagnosis apparatus 100 may register the 2D ultrasound image to the 3D ultrasound image based on a value of at least one parameter for candidate follicles detected in the 3D ultrasound image.

The ultrasound diagnosis apparatus 100 may guide, based on a result of the registering, a position of at least one candidate follicle from which an oocyte is to be extracted on the 2D ultrasound image.

As shown in FIG. 7, the ultrasound diagnosis apparatus 100 may obtain a 3D image including an ovarian region. The ultrasound diagnosis apparatus 100 may detect candidate follicles in a 3D ultrasound image based on a parameter used for extracting oocytes. The ultrasound diagnosis apparatus 100 may obtain a 3D ultrasound image 740 in which only candidate follicles are detected. Furthermore, the ultrasound diagnosis apparatus 100 may display 2D ultrasound images 710, 720, and 730 respectively corresponding to predetermined cross-sections of an ovarian region.

The ultrasound diagnosis apparatus 100 may obtain in real-time a 2D ultrasound image 750 corresponding to a predetermined cross-section of the ovarian region. The ultrasound diagnosis apparatus 100 may register the 2D ultrasound image to the 3D ultrasound image 740 based on candidate follicles detected in the 3D ultrasound image 740. The ultrasound diagnosis apparatus 100 may display, based on a result of the registering, a position of at least one candidate follicle from which an oocyte is to be extracted.

A user may identify a position of a candidate follicle displayed in the 2D ultrasound image 750 and extract an oocyte from the candidate follicle via an oocyte extractor of the ultrasound diagnosis apparatus 100.

When a first oocyte is extracted from a first candidate follicle among the at least one candidate follicle, the ultrasound diagnosis apparatus 100 may display on the 2D ultrasound image 750 information indicating that the first oocyte has been extracted from the first candidate follicle.

For example, referring to the ultrasound image 750 of FIG. 7, the ultrasound diagnosis apparatus 100 may display a contour line of the first candidate follicle from which the first oocyte has been extracted as a bold line, and display an area of the first candidate follicle shaded. The ultrasound diagnosis apparatus 100 may display a candidate follicle from which an oocyte has been extracted to be distinguished from a candidate follicle from which an oocyte has not been extracted, thereby allowing the user to extract an oocyte from a candidate follicle more accurately and promptly.

The ultrasound diagnosis apparatus 100 may display the 2D ultrasound images 710, 720, and 730 respectively corresponding to the predetermined cross-sections of the ovarian region and the 3D ultrasound image 740 including the ovarian region. Furthermore, the ultrasound diagnosis apparatus 100 may display the 2D ultrasound image 750 obtained in real-time, together with the 2D ultrasound images 710, 720, and 730 and the 3D ultrasound image 740.

When the first oocyte is extracted from the first candidate follicle, the ultrasound diagnosis apparatus 100 may display information indicating that the first oocyte has been extracted from the first candidate follicle on the 2D ultrasound images 710, 720, and 730, respectively. Referring to the ultrasound images 710, 720, and 730 of FIG. 7, the ultrasound diagnosis apparatus 100 may display a contour line of the first candidate follicle as a bold line and display an area of the first candidate follicle shaded.

Furthermore, unlike in FIG. 7, the ultrasound diagnosis apparatus 100 may respectively display on the 2D ultrasound images 710, 720, and 730 a contour line or color of the first candidate follicle differently from a contour line or color of another candidate follicle from which an oocyte has not been extracted, such that the first candidate follicle is distinguished from the other candidate follicle.

Furthermore, the ultrasound diagnosis apparatus 100 may display, on the 3D ultrasound image 740, the first candidate follicle from which the first oocyte has been extracted to be distinguished from the other candidate follicles from which oocytes have not been extracted. In other words, the ultrasound diagnosis apparatus 100 may display on the 3D ultrasound image 740 a contour line or color of the first candidate follicle differently from contour lines or colors of candidate follicles from which oocytes have not been extracted.

The ultrasound diagnosis apparatus 100 may display in real-time a candidate follicle from which an oocyte has been extracted on the 2D ultrasound images 710, 720, and 730 and the 3D ultrasound image 740 in such a manner as to be distinguished from a candidate follicle from which an oocyte has not been extracted, thereby preventing the user from performing again an extraction procedure on the candidate follicle from which the oocyte has been extracted.

Figure 8:
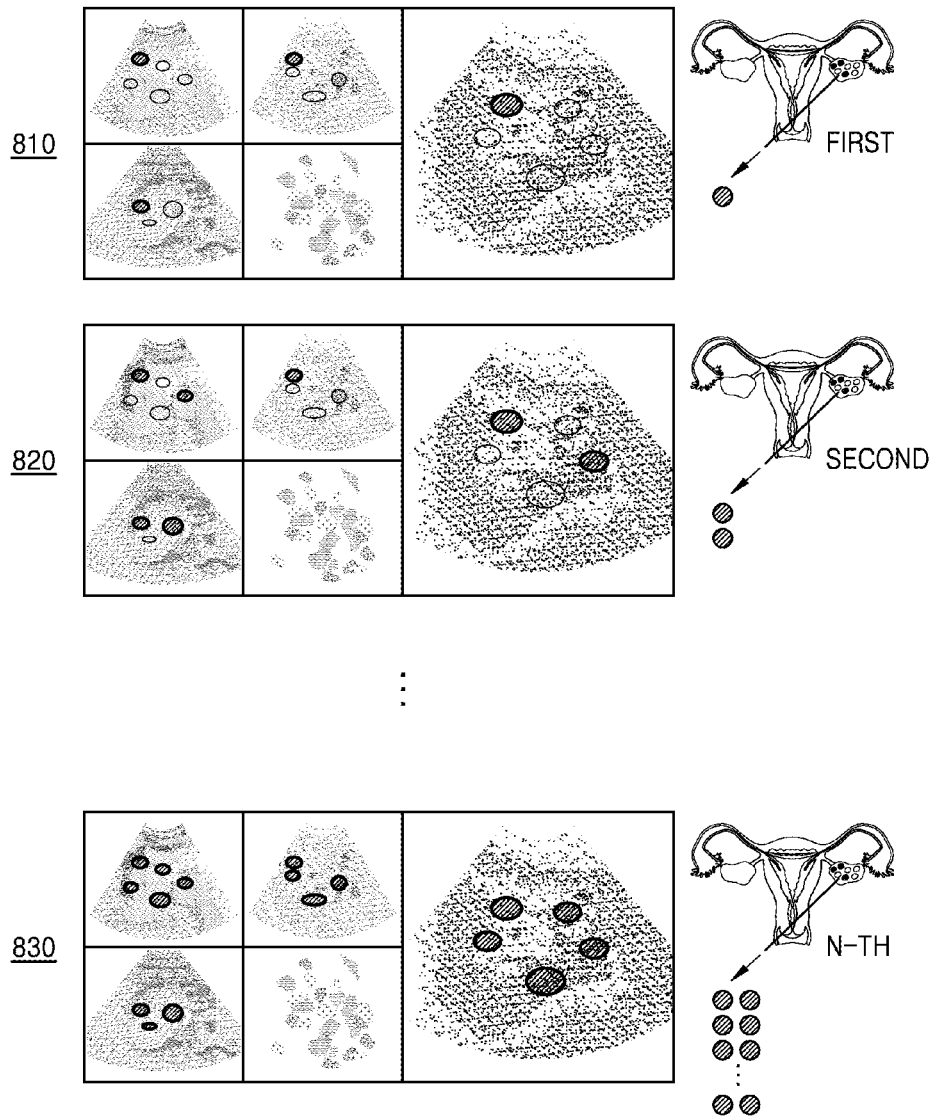
FIG. 8 illustrates a process of extracting an oocyte from each candidate ovarian follicle, according to an embodiment.

FIG. 8 illustrates a process of extracting an oocyte from each candidate follicle, according to an embodiment.

The ultrasound diagnosis apparatus 100 may display in real-time a 2D ultrasound image corresponding to a predetermined cross-section of an ovarian region. The probe 20 of the ultrasound diagnosis apparatus 100 may be kept in a fixed state until oocytes are all extracted from candidate follicles in the 2D ultrasound image.

Each time an oocyte is extracted from each of the candidate follicles in the 2D ultrasound image, the ultrasound diagnosis apparatus 100 may update and display information indicating that the oocyte has been extracted from the candidate follicle.

Referring to an image 810 of FIG. 8, the ultrasound diagnosis apparatus 100 may respectively display candidate follicles from which oocytes are to be extracted in 2D ultrasound images. A user may select a first candidate follicle from among candidate follicles in a 2D ultrasound image and extract a first oocyte from the first candidate follicle. When the first oocyte is extracted from the first candidate follicle, the ultrasound diagnosis apparatus 100 may display the first candidate follicle to be distinguished from candidate follicles from which oocytes have not been extracted. As shown in the image 810 of FIG. 8, the ultrasound diagnosis apparatus 100 display, on each of the 2D ultrasound images, a contour line of the first candidate follicle as a bold line and an area of the first candidate follicle shaded. Furthermore, the ultrasound diagnosis apparatus 100 may display, on a 3D ultrasound image, the first candidate follicle from which the first oocyte has been extracted to be distinguished from the other candidate follicles from which oocytes have not been extracted.

Referring to the image 820 of FIG. 8, after extracting the first oocyte from the first candidate follicle, the user may then select a second candidate follicle from among the other candidate follicles from which oocytes have not been extracted. The user may extract a second oocyte from the second candidate follicle. When the second oocyte is extracted from the second candidate follicle, the ultrasound diagnosis apparatus 100 may distinctively display the second candidate follicle as a candidate follicle from which an oocyte has been extracted. As shown in the image 820 of FIG. 8, the ultrasound diagnosis apparatus 100 may display, on each of the 2D ultrasound images, a contour line of the second candidate follicle as a bold line and an area of the second candidate follicle shaded. Similarly, the ultrasound diagnosis apparatus 100 may display, on a 3D ultrasound image, the second candidate follicle as a candidate follicle from which an oocyte has been extracted.

The user may respectively extract oocytes from candidate follicles in a 2D ultrasound image obtained in real-time while examining candidate follicles from which oocytes have been extracted and from which oocytes have not been extracted in the 2D ultrasound image. When oocytes are respectively extracted from candidate follicles in the 2D ultrasound image, as shown in an image 830 of FIG. 8, the ultrasound diagnosis apparatus 100 may then display contour lines of the candidate follicles from which the oocytes have been extracted as bold lines and areas of the candidate follicles shaded. Furthermore, the ultrasound diagnosis apparatus 100 may also display, on a 3D ultrasound image, the candidate follicles in the 2D ultrasound image to be distinguished from candidate follicles from which oocytes have not been extracted.

When oocytes are extracted from all the candidate follicles in a 2D ultrasound image obtained in real-time, the ultrasound diagnosis apparatus 100 may display information indicating that all of the oocytes have been extracted from a first cross-section of an ovarian region corresponding to the 2D ultrasound image. The ultrasound diagnosis apparatus 100 may also guide extraction of oocytes from a second cross-section of the ovarian region.

Figure 9:
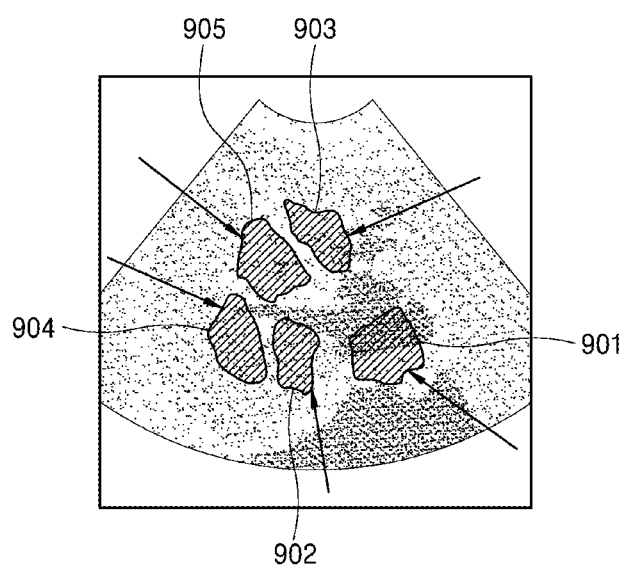
FIG. 9 illustrates a process of guiding a route along which an oocyte is to be extracted, based on position information of a structure within an ovarian region, according to an embodiment.

FIG. 9 illustrates a process of guiding a route along which an oocyte is to be extracted, based on position information of a structure within an ovarian region, according to an embodiment.

Follicles may be dispersed in a certain region of an ovary. An oocyte extractor such as a needle may be used to extract oocytes from follicles. Because a certain structure exists within or outside the ovary, the user needs to avoid the certain structure in order to extract an oocyte from a follicle.

The ultrasound diagnosis apparatus 100 may acquire position information of at least one structure based on an anatomical structure within the ovarian region. The ultrasound diagnosis apparatus 100 may guide, based on the position information of the at least one structure, a route along which an oocyte is to be extracted from at least one candidate follicle.

Referring to FIG. 9, the ultrasound diagnosis apparatus 100 may obtain in real-time a 2D ultrasound image corresponding to a predetermined cross-section of the ovarian region. The ultrasound diagnosis apparatus 100 may display candidate follicles 901 through 905 on the 2D ultrasound image based on a 3D ultrasound image in which candidate follicles, from which mature oocytes are more likely to be extracted, are detected. In this case, the candidate follicles 901 through 905 may be some of the candidate follicles detected in the 3D ultrasound image.

As shown in FIG. 9, the ultrasound diagnosis apparatus 100 may acquire, based on the position information of the at least one structure within the ovarian region, a route along which an oocyte extractor is guided to reach a candidate follicle without contacting a certain structure. The ultrasound diagnosis apparatus 100 may display routes along which the oocyte extractor may respectively reach the candidate follicles 901 through 905. The routes shown in FIG. 9 are merely an example, and an oocyte may be extracted along another route.

Figure 10:
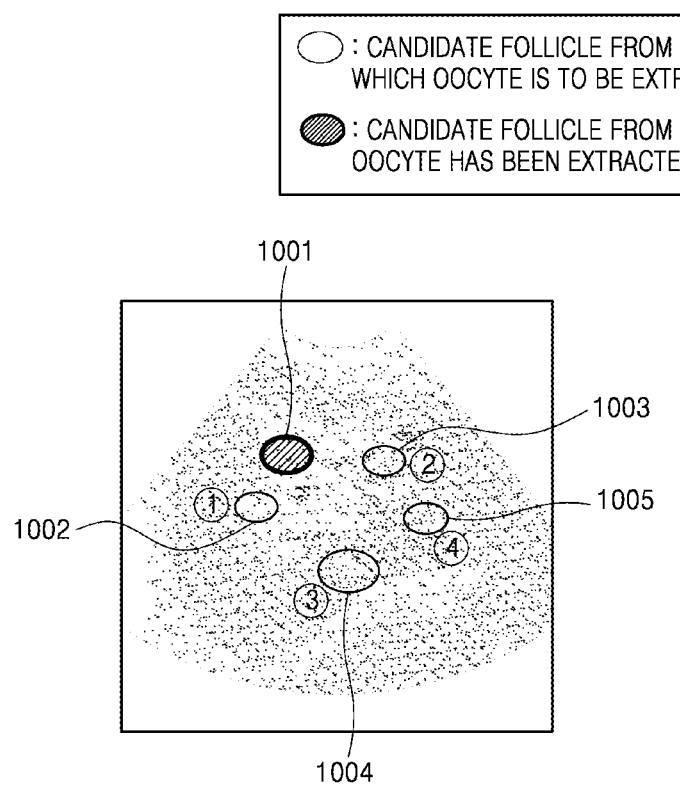
FIG. 10 illustrates a process by which an ultrasound diagnosis apparatus extracts oocytes from candidate ovarian follicles, according to an embodiment.

FIG. 10 illustrates a process by which the ultrasound diagnosis apparatus 100 extracts oocytes from candidate follicles, according to an embodiment.

As oocytes are extracted from candidate follicles in a 2D ultrasound image, the ultrasound diagnosis apparatus 100 may display, on the 2D ultrasound image, tracking information indicating tracking of candidate follicles from which oocytes have been extracted and from which oocytes have not been extracted.

For example, the user may extract via an oocyte extractor a first oocyte from a first candidate follicle 1001 among candidate follicles, i.e., first through fifth candidate follicles 1001 through 1005 in the 2D ultrasound image. The ultrasound diagnosis apparatus 100 may display a contour line of the first candidate follicle 1001 as a bold line and an area of the first candidate follicle 1001 shaded.

Furthermore, after the first oocyte has been extracted from the first candidate follicle 1001 from among the first through fifth candidate follicles 1001 through 1005, the ultrasound diagnosis apparatus 100 may guide a position of the second candidate follicle 1002 from which a second oocyte is subsequently to be extracted in the 2D ultrasound image. For example, the ultrasound diagnosis apparatus 100 may display a reference number ① near the second candidate follicle 1002.

In this case, the ultrasound diagnosis apparatus 100 may respectively display reference numbers ② through ⑤ near the second through fifth candidate follicles 1002 through 1005. For example, the order of the reference numbers may be arbitrarily determined. Furthermore, the order of the reference numbers may be determined in the order of a size of a candidate follicle, but is not limited thereto. In other words, the ultrasound diagnosis apparatus 100 may determine and display the order in which oocytes are to be extracted from candidate follicles in the 2D ultrasound image. By extracting an oocyte from a candidate follicle according to the determined order, the user may perform a more accurate and prompt extraction procedure.

Furthermore, after the second oocyte has been extracted from the second candidate follicle 1002, the ultrasound diagnosis apparatus 100 may guide a position of the third candidate follicle 1003 from which a third oocyte is subsequently to be extracted in the 2D ultrasound image. Similarly, the ultrasound diagnosis apparatus 100 may respectively assign reference numbers to the third through fifth candidate follicles 1003 through 1005 from which oocytes have not been extracted and display the assigned reference numbers.

Figure 11:
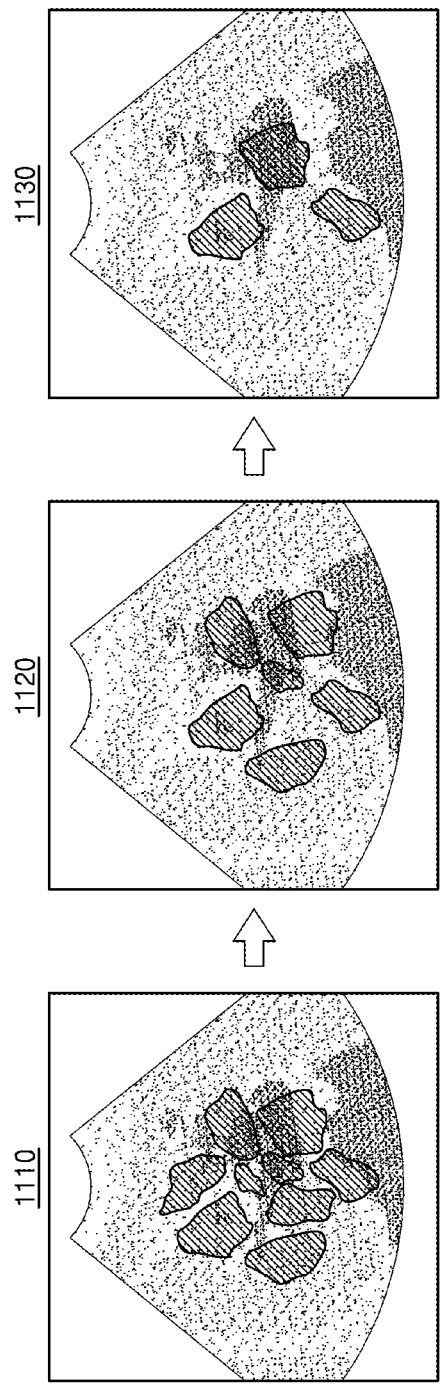
FIG. 11 illustrates a process of obtaining a 2D ultrasound image used for extracting an oocyte from a candidate ovarian follicle, according to an embodiment.

FIG. 11 illustrates a process of obtaining a 2D ultrasound image used for extracting an oocyte from a candidate follicle, according to an embodiment.

The ultrasound diagnosis apparatus 100 may determine, based on positions of a plurality of candidate follicles detected in a 3D ultrasound image, a priority order of cross-sections according to a decreasing order of probability of detecting a candidate follicle from an ovarian region.

For example, the ultrasound diagnosis apparatus 100 may determine a first cross-section having the highest probability of detecting a candidate follicle as a first priority. The ultrasound diagnosis apparatus 100 may display positions of candidate follicles on a 2D ultrasound image 1110 corresponding to a first cross-section. The user may respectively extract oocytes from the candidate follicles while examining the positions of the candidate follicles. Each time an oocyte is extracted from a candidate follicle, the ultrasound diagnosis apparatus 100 may display, on the 2D ultrasound image 1110 and the 3D ultrasound image, a candidate follicle from which an oocyte has been extracted to be distinguished from a candidate follicle from which an oocyte has not been extracted.

When oocytes are all extracted from candidate follicles in the 2D ultrasound image 1110, the ultrasound diagnosis apparatus 100 may then determine a second cross-section having the second highest probability of detecting a candidate follicle. The ultrasound diagnosis apparatus 100 may display positions of candidate follicles on a 2D ultrasound image 1120 corresponding to the second cross-section. The user may respectively extract oocytes from the candidate follicles while examining the positions of the candidate follicles.

Similarly, when oocytes are all extracted from candidate follicles in the 2D ultrasound image 1120, the ultrasound diagnosis apparatus 100 may then determine a third cross-section having the third highest probability of detecting a candidate follicle. The ultrasound diagnosis apparatus 100 may display positions of candidate follicles on a 2D ultrasound image 1130 corresponding to the third cross-section. The user may respectively extract oocytes from the candidate follicles while examining the positions of the candidate follicles.

In other words, the ultrasound diagnosis apparatus 100 may determine a priority order of cross-sections according to a decreasing order of probability of detecting a candidate follicle. The ultrasound diagnosis apparatus 100 may obtain a 2D ultrasound image corresponding to a cross-section according to the priority order and guide extraction of oocytes from candidate follicles based on the 2D ultrasound image.

Figure 12:
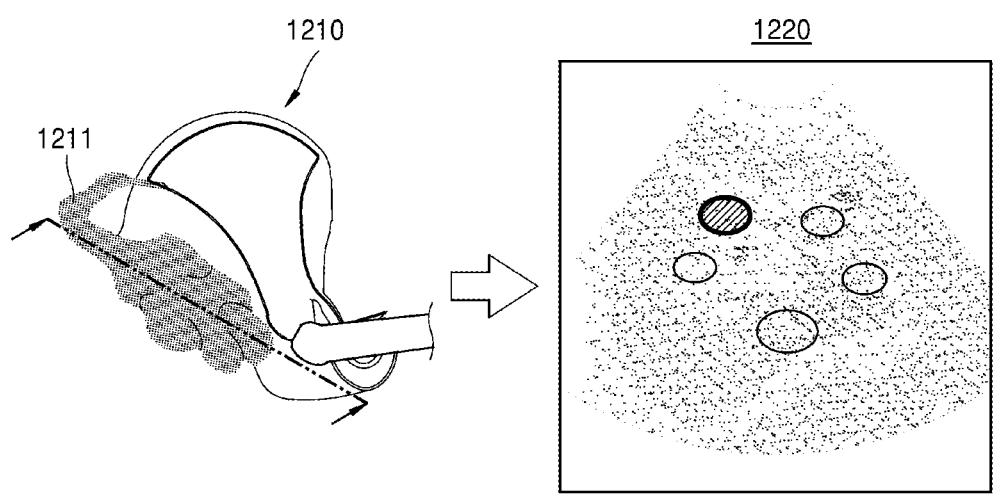
FIG. 12 illustrates a process of displaying a 2D ultrasound image based on information about candidate ovarian follicles in a 3D ultrasound image, according to an embodiment.

FIG. 12 illustrates a process of displaying a 2D ultrasound image based on information about candidate follicles in a 3D ultrasound image, according to an embodiment.

The ultrasound diagnosis apparatus 100 may obtain a 3D ultrasound image 1210 including an ovarian region. The ultrasound diagnosis apparatus 100 may detect, based on a parameter used for extracting an oocyte, candidate follicles from which mature oocytes are more likely to be extracted in the 3D ultrasound image 1210. The ultrasound diagnosis apparatus 100 may acquire, based on a value of a parameter, follicle information about at least one of a position, a size, and a volume of each of the candidate follicles.

In addition, the ultrasound diagnosis apparatus 100 may obtain a 2D ultrasound image 1220 corresponding to a predetermined cross-section of the ovarian region in real-time. The ultrasound diagnosis apparatus 100 may register the 2D ultrasound image 1220 with the 3D ultrasound image 1210 based on a value of a parameter for the candidate follicles detected in the 3D ultrasound image 1210. The ultrasound diagnosis apparatus 100 may determine positions of the candidate follicles in the 2D ultrasound image 1220 based on a result of the registering and display the candidate follicles.

Furthermore, the ultrasound diagnosis apparatus 100 may display, on the 3D ultrasound image 1210, a position of a cross-section 1211 corresponding to the 2D ultrasound image 1220.

Figure 13:
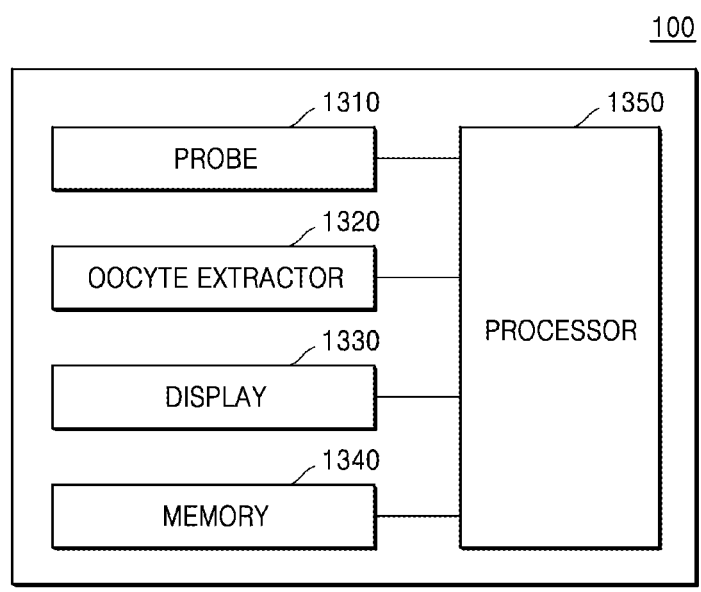
FIG. 13 is a block diagram of a configuration of an ultrasound diagnosis apparatus according to an embodiment.

FIG. 13 is a block diagram of a configuration of an ultrasound diagnosis apparatus 100 according to an embodiment. The ultrasound diagnosis apparatus 100 may include a probe 1310, an oocyte extractor 1320, a display 1330, a memory 1340, and a processor 1350. However, all the components shown in FIG. 13 are not essential components. The ultrasound diagnosis apparatus 100 may include more or fewer components than those shown in FIG. 13. Configurations and operations of the above-described components will now be described in detail.

The probe 1310 may include a plurality of transducers that convert ultrasound signals into electrical signals or vice versa. In other words, the probe 1310 may include a transducer array consisting of a plurality of transducers, and the transducers may be arranged in a one-dimensional (1D) or 2D array. Each of the transducers generates ultrasound signals separately or simultaneously. An ultrasound signal transmitted by each transducer is reflected off a discontinuous impedance surface within an object. Each transducer may convert a received reflected echo signal into an electrical reception signal. The probe 1310 may transmit ultrasound signals to an ovarian region of the object and receive echo signals reflected therefrom. In this case, the object may be a human.

The oocyte extractor 1320 may extract an oocyte from a follicle. Furthermore, the oocyte extractor 1320 may include a needle used for extracting an oocyte from a follicle. The oocyte extractor 1320 may also be mounted to the probe 1310 to be movable in conjunction with the probe 1310.

The display 1330 displays a predetermined screen. In detail, the display 1330 may display a predetermined screen according to control by the processor 1350. The display 1330 includes a display panel on which an ultrasound image may be displayed.

The memory 1340 may store a program for executing a method of operating the ultrasound diagnosis apparatus 100. Furthermore, the memory 1340 may store code representing a method of operating the ultrasound diagnosis apparatus 100.

The memory 1340 may store 2D and 3D ultrasound images. The memory 1340 may also store pieces of information acquired from the 2D and 3D ultrasound images.

For example, information acquired from 2D and 3D ultrasound images may include information about at least one of a position, a size, and a volume of a candidate follicle, a parameter used for extracting an oocyte, and a value of the parameter.

The processor 1350 may obtain a 3D ultrasound image including an ovarian region.

The processor 1350 may detect, based on at least one parameter used for extracting a certain oocyte, a plurality of candidate follicles from which mature oocytes are more likely to be extracted in a 3D ultrasound image.

For example, the processor 1350 may acquire a value of at least one parameter from the 3D ultrasound image. In this case, the at least one parameter may be a parameter used for measuring at least one of a size of an ovary and a length and a volume of a follicle, but is not limited thereto. The ultrasound diagnosis apparatus 100 may detect a follicle for which a value of at least one parameter satisfies a preset range as a candidate follicle.

The processor 1350 may register a 2D ultrasound image corresponding to a first cross-section of an ovarian region to a 3D ultrasound image.

The processor 1350 may register the 2D ultrasound image to the 3D ultrasound image based on a value of at least one of parameter for a plurality of candidate follicles detected in the 3D ultrasound image.

The processor 1350 may register the 2D ultrasound image to the 3D ultrasound image based on information about candidate follicles detected in the 3D ultrasound image, thereby allowing accurate and prompt tracking of positions of the candidate follicles. In addition, registering between the 2D and 3D ultrasound images may be performed based on a value of a parameter in the 3D ultrasound image and a sensor.

The processor 1350 may guide, based on a result of the registering, a position of at least one candidate follicle from which an oocyte is to be extracted in the 2D ultrasound image.

For example, the processor 1350 may identify, based on a result of the registering, a position of at least one candidate follicle from which an oocyte is to be extracted in the 2D ultrasound image. The display 1330 may display the position of the at least one candidate follicle. When a first oocyte is extracted from a first candidate follicle among the at least one candidate follicle, the processor 1350 may control the display 1330 to display information indicating that the first oocyte has been extracted from the first candidate follicle on the 2D ultrasound image.

For example, the display 1330 may display a contour line or color of the first candidate follicle differently from a contour line or color of another candidate follicle from which an oocyte has not been extracted, such that the first candidate follicle is distinguished from the other candidate follicle.

For example, as an oocyte is extracted from the at least one candidate follicle in the 2D ultrasound image, the display 1330 may display, on the 2D ultrasound image, tracking information indicating tracking of candidate follicles from which oocytes have been extracted and from which oocytes have not been extracted.

For example, the processor 1350 may acquire position information of at least one structure based on an anatomical structure within the ovarian region. In this case, the at least one structure may be a cyst, an intima, a vessel, etc., but is not limited thereto. The processor 1350 may identify an anatomical structure within the ovarian region based on the 3D ultrasound image and acquire position information of at least one structure based on the anatomical structure. The processor 1350 may guide, based on the position information of the at least one structure, a route along which an oocyte is to be extracted from the at least one candidate follicle.

For example, after the first oocyte has been extracted from the first candidate follicle from among the at least one candidate follicle, the processor 1350 may then control the display 1330 to display guide information for guiding a position of a second candidate follicle from which a second oocyte is subsequently to be extracted in the 2D ultrasound image.

In addition, as an oocyte is extracted from the at least one candidate follicle in the 2D ultrasound image, the ultrasound diagnosis apparatus 100 may display a plurality of candidate follicles on the 3D ultrasound image in such a manner that candidate follicles where oocytes have been extracted are distinguished from candidate follicles where oocytes have not been extracted.

Furthermore, the display 1330 may display, on a 3D ultrasound image, a position of a first cross-section corresponding to a 2D ultrasound image.

Furthermore, the processor 1350 may determine, based on positions of a plurality of candidate follicles, a priority order of cross-sections according to a decreasing order of probability of detecting a candidate follicle from the ovarian region. The ultrasound diagnosis apparatus 100 may obtain 2D ultrasound images according to the priority order of cross-sections.

The ultrasound diagnosis apparatuses 100 described above may be implemented using hardware components, software components, and/or a combination thereof. For example, the apparatuses and components illustrated in the embodiments may be implemented using one or more general-purpose or special-purpose computers, such as a processor, a controller, an arithmetic logic unit (ALU), a digital signal processor, a microcomputer, a field programmable array (FPA), a programmable logic unit (PLU), a microprocessor, or any other device capable of responding to and executing instructions.

A processing device may run an operating system (OS) and one or more software applications running on the OS. The processing device may also access, store, manipulate, process, and create data in response to execution of software.

Although a single processing device may be illustrated for convenience, those of ordinary skill in the art will appreciate that a processing device may include a plurality of processing elements and/or a plurality of types of processing elements. For example, a processing device may include one or a plurality of processors and a controller. In addition, the processing device may have different processing configurations such as parallel processors.

Software may include a computer program, a piece of code, a command, or one or more combinations thereof and independently or collectively instruct or configure the processing device to operate as desired.

Software and/or data may be embodied permanently or temporarily in any type of machine, component, physical equipment, virtual equipment, computer storage medium or device, or in a transmitted signal wave so as to be interpreted by the processing device or to provide commands or data to the processing device. The software may also be distributed over network-coupled computer systems so that the software is stored and executed in a distributed fashion. The software and data may be stored in one or more computer-readable recording media.

The methods according to the embodiments may be implemented in the form of program instructions that may be executed through various computer devices and be recorded on non-transitory computer-readable recording media. The computer-readable recording media may also include, alone or in combination, program instructions, data files, data structures, and the like. The program instructions recorded on the non-transitory computer-readable recording media may be designed and configured specially for the embodiments or be known and available to those of ordinary skill in computer software.

Examples of non-transitory computer-readable recording media include magnetic media such as hard disks, floppy disks, and magnetic tape, optical media such as CD-ROM discs and DVDs, magneto-optical media such as floptical discs, and hardware devices that are specially configured to store and perform program instructions, such as ROM, RAM, flash memory, and the like.

Examples of program instructions include not only machine code made by a compiler but also high-level language code to be executed in a computer by using an interpreter.

The above-described hardware devices may be configured to act as one or more software modules in order to perform operations according to the embodiments, or vice versa.

While one or more embodiments have been described with reference to the figures, it will be understood by those of ordinary skill in the art that various modifications and changes in form and details may be made from the above descriptions without departing from the spirit and scope as defined by the following claims. For example, adequate effects may be achieved even if the above techniques are performed in a different order than that described above, and/or the aforementioned elements, such as systems, structures, devices, or circuits, are combined or coupled in different forms and modes than those described above or are replaced or supplemented by other components or their equivalents.

Thus, the scope of the disclosure is defined not by the above-described embodiments but by the appended claims and their equivalents.

What is claimed is:

1. A method of operating an ultrasound diagnosis apparatus, the method comprising:
    obtaining a three-dimensional ultrasound image including an ovarian region;
    detecting, based on at least one parameter used for extracting a particular oocyte, a plurality of candidate ovarian follicles from which mature oocytes are more likely to be extracted in the three-dimensional ultrasound image;
    obtaining a two-dimensional ultrasound image corresponding to a first cross-section of the ovarian region in real time;
    registering the two-dimensional ultrasound image to the three-dimensional ultrasound image based on a value of at least one parameter for a plurality of candidate follicles detected in the three-dimensional ultrasound image; and
    guiding, based on a result of the registering, a position of at least one candidate ovarian follicle from which an oocyte is to be extracted in the two-dimensional ultrasound image; and
    displaying, as the oocyte is extracted from the at least one candidate ovarian follicle in the two-dimensional ultrasound image, the plurality of candidate ovarian follicles on the three-dimensional ultrasound image in such a manner that candidate ovarian follicles where oocytes have been extracted are distinguished from candidate ovarian follicles where oocytes have not been extracted.

2. The method of claim 1, wherein the guiding of the position of the at least one candidate ovarian follicle in the two-dimensional ultrasound image comprises:
    displaying, based on the result of the registering, the position of the at least one candidate ovarian follicle from which the oocyte is to be extracted in the two-dimensional ultrasound image; and
    displaying, when a first oocyte is extracted from a first candidate ovarian follicle among the at least one candidate ovarian follicle, information indicating that the first oocyte has been extracted from the first candidate ovarian follicle on the two-dimensional ultrasound image.

3. The method of claim 2, wherein the displaying of the information indicating that the first oocyte has been extracted from the first candidate ovarian follicle on the two-dimensional ultrasound image comprises displaying a contour line or color of the first candidate ovarian follicle differently from a contour line or color of a candidate ovarian follicle from which an oocyte has not been extracted, such that the first candidate ovarian follicle is distinguished from the candidate ovarian follicle.

4. The method of claim 1, wherein the detecting of the plurality of candidate ovarian follicles in the three-dimensional ultrasound image comprises:
    acquiring a value of the at least one parameter from the three-dimensional ultrasound image; and detecting an ovarian follicle for which the value of the at least one parameter satisfies a predetermined range as a candidate ovarian follicle.

5. The method of claim 1, wherein the at least one parameter is a parameter used for measuring at least one of a size of an ovary and a length and a volume of an ovarian follicle.

6. The method of claim 1, wherein the guiding of the position of the at least one candidate ovarian follicle in the two-dimensional ultrasound image comprises:
   acquiring position information of at least one structure based on an anatomical structure within the ovarian region; and
   guiding, based on the position information of the at least one structure, a route along which the oocyte is to be extracted from the at least one candidate ovarian follicle.

7. The method of claim 1, further comprising displaying, as the oocyte is extracted from the at least one candidate ovarian follicle in the two-dimensional ultrasound image, the plurality of candidate ovarian follicles on the three-dimensional ultrasound image in such a manner that candidate ovarian follicles where oocytes have been extracted are distinguished from candidate ovarian follicles where oocytes have not been extracted.

8. The method of claim 1, further comprising displaying, on the three-dimensional ultrasound image, a position of the first cross-section corresponding to the two-dimensional ultrasound image.

9. The method of claim 1, wherein the guiding of the position of the at least one candidate ovarian follicle in the two-dimensional ultrasound image comprises guiding, after a first oocyte is extracted from a first candidate ovarian follicle among the at least one candidate ovarian follicle, a position of a second candidate ovarian follicle from which a second oocyte is subsequently to be extracted in the two-dimensional ultrasound image.

10. The method of claim 1, further comprising:
   determining, based on positions of the plurality of candidate follicles, a priority order of cross-sections according to a decreasing order of probability of detecting a candidate follicle from the ovarian region; and
   obtaining a two-dimensional ultrasound image according to the priority order of the cross-sections.

11. An ultrasound diagnosis apparatus comprising:
   a probe configured to transmit ultrasound signals to an ovarian region of an object and receive echo signals reflected from the ovarian region;
   a processor configured to obtain a three-dimensional ultrasound image including the ovarian region based on the echo signals, detect, based on at least one parameter used for extracting a particular oocyte, a plurality of candidate ovarian follicles from which mature oocytes are more likely to be extracted in the three-dimensional ultrasound image,
   obtain a two-dimensional ultrasound image corresponding to a first cross-section of the ovarian region in real time;
   register the two-dimensional ultrasound image to the three-dimensional ultrasound image based on a value of at least one parameter for a plurality of candidate follicles detected in the three-dimensional ultrasound image, and guide, based on a result of the registering, a position of at least one candidate ovarian follicle from which an oocyte is to be extracted in the two-dimensional ultrasound image;
   a display displaying information for guiding the position of the at least one candidate ovarian follicle and displaying, as the oocyte is extracted from the at least one candidate ovarian follicle in the two-dimensional ultrasound image, the plurality of candidate ovarian follicles on the three-dimensional ultrasound image in such a manner that candidate ovarian follicles where oocytes have been extracted are distinguished from candidate ovarian follicles where oocytes have not been extracted; and
   an oocyte extractor configured to extract the oocyte from the at least one candidate ovarian follicle.

12. The ultrasound diagnosis apparatus of claim 11, wherein the processor is further configured to control the display to:
   display, based on the result of the registering, the position of the at least one candidate ovarian follicle from which the oocyte is to be extracted in the two-dimensional ultrasound image; and
   display, when a first oocyte is extracted from a first candidate ovarian follicle among the at least one candidate ovarian follicle via the oocyte extractor, information indicating that the first oocyte has been extracted from the first candidate ovarian follicle on the two-dimensional ultrasound image.

13. The ultrasound diagnosis apparatus of claim 12, wherein the processor is further configured to control the display to display a contour line or color of the first candidate ovarian follicle differently from a contour line or color of a candidate ovarian follicle from which an oocyte has not been extracted, such that the first candidate ovarian follicle is distinguished from the candidate ovarian follicle.

14. The ultrasound diagnosis apparatus of claim 11, wherein the processor is further configured to acquire a value of the at least one parameter from the three-dimensional ultrasound image and detect an ovarian follicle for which the value of the at least one parameter satisfies a predetermined range as a candidate ovarian follicle.

15. The ultrasound diagnosis apparatus of claim 11, wherein the processor is further configured to control the display to display, as the oocyte is extracted via the oocyte extractor from the at least one candidate ovarian follicle in the two-dimensional ultrasound image, the plurality of candidate ovarian follicles on the three-dimensional ultrasound image in such a manner that candidate ovarian follicles where oocytes have been extracted are distinguished from candidate ovarian follicles where oocytes have not been extracted.

16. A computer program stored in a computer-readable recording medium to perform a method in combination with an ultrasound diagnosis apparatus, the method comprising:
   obtaining a three-dimensional ultrasound image including an ovarian region;
   detecting, based on at least one parameter used for extracting a particular oocyte, a plurality of candidate ovarian follicles from which mature oocytes are more likely to be extracted in the three-dimensional ultrasound image;
   obtaining a two-dimensional ultrasound image corresponding to a first cross-section of the ovarian region in real time;
   registering the two-dimensional ultrasound image to the three-dimensional ultrasound image based on a value of at least one parameter for a plurality of candidate follicles detected in the three-dimensional ultrasound image;

guiding, based on a result of the registering, a position of at least one candidate ovarian follicle from which an oocyte is to be extracted in the two-dimensional ultrasound image; and displaying, as the oocyte is extracted from the at least one candidate ovarian follicle in the two-dimensional ultrasound image, the plurality of candidate ovarian follicles on the three-dimensional ultrasound image in such a manner that candidate ovarian follicles where oocytes have been extracted are distinguished from candidate ovarian follicles where oocytes have not been extracted.

\* \* \* \* \*